United States Patent [19]

Lam

[11] 4,303,753

[45] Dec. 1, 1981

[54] METHOD AND DEVICE FOR THE SEMIQUANTITATIVE DETERMINATION OF GLUCOSE IN AQUEOUS FLUIDS

[75] Inventor: Charles T. W. Lam, Elkhart, Ind.

[73] Assignee: Miles Laboratories, Inc., Elkhart, Ind.

[21] Appl. No.: 132,281

[22] Filed: Mar. 20, 1980

[51] Int. Cl.$^3$ .......................... C12Q 1/54; C12Q 1/28; G01N 1/48

[52] U.S. Cl. ........................................ 435/14; 435/28; 435/805; 422/56

[58] Field of Search .................. 435/14, 28, 805, 810; 422/56; 23/230 B

[56] References Cited

U.S. PATENT DOCUMENTS

| | | | |
|---|---|---|---|
| 3,630,957 | 12/1971 | Rey et al. ............................ | 435/805 |
| 3,814,668 | 6/1974 | Blake et al. .......................... | 435/14 |
| 3,971,702 | 7/1976 | MacKawa et al. .................. | 435/14 |
| 3,992,158 | 11/1976 | Przybylowicz et al. ............ | 435/14 |

FOREIGN PATENT DOCUMENTS 2546252  4/1976  Fed. Rep. of Germany ........ 422/56

*Primary Examiner*—Thomas G. Wiseman
*Attorney, Agent, or Firm*—Jerome L. Jeffers

[57] ABSTRACT

Disclosed is an improved method for the preparation of test strips for the semiquantitative determination of glucose in aqueous fluids, e.g. urine. The test strips are comprised of a bibulous carrier impregnated with glucose oxidase, a substance having peroxidative activity and a water soluble iodide salt. The device is coated with the residue of a solution of a film forming material which, pursuant to the improvement disclosed herein, is obtained by saturating the strip with a solution containing about 1.75 to about 4.55 grams (g)/100 milliliters (ml) of ethyl cellulose in an appropriate solvent.

15 Claims, No Drawings

METHOD AND DEVICE FOR THE SEMIQUANTITATIVE DETERMINATION OF GLUCOSE IN AQUEOUS FLUIDS

BACKGROUND OF THE INVENTION

The detection of the concentration of glucose in urine is of great importance to diabetic individuals who must control their blood sugar level. Because continued control of blood sugar level is so important, a test device for the determination of glucose concentration in urine must be rapid and simple enough for the individual to use with ease and it must be quantitative enough to accurately measure increments of glucose concentration and thereby differentiate between various medical conditions.

A novel and very effective device for the quick and convenient determination of urine glucose concentration is disclosed in U.S. Pat. No. 3,814,668 (the '668 patent), issued June 4, 1974. This patent discloses a test strip which comprises a carrier member impregnated with glucose oxidase, a peroxidative active substance and a water soluble iodide salt which is coated with a hydrophobic, semi-permeable membrane such as ethyl cellulose.

The semi-permeable membrane coating is designed to prevent the retention of excess liquid sample on the test device and therefore provide more reliable semi-quantititive results. The patent teaches that a reasonably wide range of concentrations of materials can be used and more specifically discloses the application of the semi-permeable membrane from a solution containing 0.5 to 1 g of film forming polymer, e.g., ethyl cellulose, per 100 ml of organic solvent.

Test strips made by the process in the '668 patent are highly effective for the intended purpose. However, a phenomenon known as "windowframing" or "edgewetting" has been observed with these strips. Windowframing may reveal itself through the development of very small isolated wet spots around the margin of the strip after dipping. In some cases, a continuous wet margin around the reacted strip may be observed. The windowframing problem is strictly a phenomenon occuring at the edge of the strips, since the strips are prepared by cutting a sheet of the bibulous carrier after it is coated. Since the wet spots or wet margin are invariably of a different color from the rest of the reagent strip, visual matching of the reacted strips to color charts becomes difficult and may possibly lead to incorrect results. One solution to the problem has been to carefully control the ethoxyl content and viscosity of the ethyl cellulose. This technique introduces an additional parameter which increases quality control and raw material procurement problems.

It would be desirable, and it is an object of this invention, to provide a novel process for the preparation of the previously described glucose test strips which eliminates the problem of windowframing.

An additional object is to provide such a process which eliminates the problem of windowframing without slowing down the test strip's reactivity to an unacceptable rate.

A further object is to provide a process which permits the use of a wider range of ethyl cellulose formulations than was possible using prior art coating techniques.

An additional object is to provide an improved test strip prepared by the process described herein.

SUMMARY OF THE INVENTION

The present invention is an improvement in the process of preparing a test device for the semi-quantitative determination of glucose in urine which process comprises impregnating a sheet of a bibulous carrier with a solution containing glucose oxidase, a substance having peroxidative activity and a water soluble iodide salt, drying the treated carrier and then saturating the carrier with an organic solution of a film-forming material, drying the carrier to leave a dry residue of the film forming material and cutting the sheet into test strips. The improvement involves the use of a solution containing from about 1.75 to about 4.55 g/100 ml of ethyl cellulose in an appropriate solvent as the organic solution of film-forming material.

DESCRIPTION OF THE INVENTION

The method of preparing the test device of the present invention and the improved performance of such a device are illustrated by the following examples in which all percentages are by weight:

EXAMPLE I

Varying Ethyl Cellulose Concentration

The following solution was prepared:
84.0 ml. stock ethylene diamine tetraacitic acid (EDTA) buffer.
1.8 g potassium iodide.
60.0 ml glucose oxidase (1054.5 International Units/ml.).
9.0 ml 10% polyvinylpyrrolidone (PVP) in water.
18.0 ml 10% Gantrez in water.
0.005 g FD&C Blue #1.
0.2 g peroxidase.

The stock EDTA buffer was prepared by mixing 19.2 g of citric acid, 93.6 g of sodium citrate and 72.0 g of Versene (tetrasodium EDTA) in 1008 ml of distilled water. The purpose of the buffer is to maintain the pH at a level of from 3.4 to 7.2 when the device is contacted with the fluid to be tested.

In operation, the enzyme glucose oxidase catalyzes the aerobic oxidation of glucose to produce gluconic acid and hydrogen peroxide. In addition to the enzyme glucose oxidase the system must include a material having peroxidative activity hence the use of peroxidase.

In addition to glucose oxidase and peroxidase, an iodide salt, in this case potassium iodide, is necessary as a chromogen. The color forming reaction is represented by the following equations:

$$\text{glucose oxidase} + \text{glucose} \rightarrow H_2O_2 + \text{gluconic acid}$$

$$\text{peroxidase} + H_2O_2 + KI \rightarrow I_2$$

$$I_2 + KI \rightarrow I_3^-$$

Further to the utilization of an iodide salt as chromogen, a second indicator substance is preferably used to provide a gradient response to the presence of various concentration of glucose in the urine to be tested. In the above formulation FD&C Blue #1 has been chosen as the second indicator.

Polyvinylpyrrolidone and Gantrez (a copolymer of methylvinylether and maleic anhydride) are used as thickening agents which also function as enzyme stabilizers.

Sheets of Whatman 3 MM paper (approximately 7.6 cm × 17.8 cm) were dipped into the solution and dried at 90°-95° C. for 10 to 15 minutes. The dried pieces of paper were then dipped into solutions of ethyl cellulose in 20/80 ethanol/toluene (v/v) in which the concentration of ethyl cellulose ranged from 0.75 to 4.55 g/100 ml. The selection of solvent is not critical provided that the material will solubilize ethyl cellulose and will evaporate from the device after application to leave a uniform residual layer of ethyl cellulose. Other suitable solvents include toluene, benzene and various combinations of toluene and ethanol.

After treatment with the ethyl cellulose solution the paper sheets were cut into strips and the test strips were evaluated for their windowframing properties and reactivities with the results of this evaluation being set out in Table I.

TABLE I

| Ethyl Cellulose Conc. (g/100 ml) | Window-framing | Reactivity |
| --- | --- | --- |
| 0.75–1.55 | obvious windowframing | good reaction |
| 1.75–3.35 | acceptable to no windowframing | good reaction |
| 3.75–4.55 | no windowframing | slower reaction |

From Table I, it can be determined that an ethyl cellulose concentration below 1.55 g/100 ml is unsatisfactory because of windowframing. At a concentration of 1.75 g/100 ml the windowframing phenomenon was observed to diminish and completely disappear as the concentration approached 3.35 g/100 ml. Thus, a minimum concentration of about 1.75 g/100 ml is necessary to provide test strips which are entirely suitable for their intended purpose. At higher concentrations of ethyl cellulose windowframing was not a problem, but as the concentration was increased the reaction slowed so that the use of a solution containing greater than about 4.55 g/100 ml would be impracticable.

The most desirable concentration range is from 2.35 to 3.35 g/100 ml since this will leave an ethyl cellulose residue thick enough to inhibit windowframing without significantly slowing down the reaction.

EXAMPLE II

Varying Ethoxyl Content Of Ethyl Cellulose

Pieces of Whatman 3 MM paper were impregnated in the first solution and dried as described in Example I. A second solution was prepared by dissolving 4.0 g/100 ml of ethyl cellulose in a 20/80 ethanol/toluene solution. The following types of ethyl cellulose obtained from Hercules, Inc. were used:

1. K-type: ethoxyl content (46.7%)
2. N-type: ethoxyl content (47.7%)
3. T-type: ethoxyl content (49.5%)

Pieces of the paper impregnated with the first solution were again impregnated in the above solutions and dried. Strip devices were prepared from these papers and evaluated for windowframing and reactivity. All three formulations showed identical reactivity and no windowframing. It can be concluded, therefore, that at an ethyl cellulose concentration of 4.0 g/100 ml, the ethoxyl content may range from 46.7% to 49.5% without fear of windowframing.

EXAMPLE III

Varying Viscosity Of Ethyl Cellulose

The experiment of Example II was repeated using the following types of ethyl cellulose obtained from Hercules, Inc.:

1. N-22: viscosity* (20); ethoxyl content (47.8%)
2. N-50: viscosity (50); ethoxyl content (47.7%)
3. N-100: viscosity (95); ethoxyl content (47.7%)
4. N-200: viscosity (206); ethoxyl content (47.6%)

*(5% W/W in 80/20 toluene/ethanol @ 25° C.)

Test strips prepared from these materials indicated no reaction differences between them and no windowframing. This result indicates that the molecular weight of the ethyl cellulose selected for use is not a limiting factor.

EXAMPLE IV

Random Lots and Types Of Ethyl Cellulose

The following samples of ethyl cellulose were used at the 3.0 g/100 ml level in 80/20 toluene/ethanol without observing any windowframing.

| Type | Ethoxyl | Viscosity | Manufacturer |
| --- | --- | --- | --- |
| N-50 | 47.7 | 50 | Hercules |
| T-50 | 49.5 | 48 | Hercules |
| T-50 | 49.3 | 51 | Hercules |
| N-7 | 47.6 | 7 | Hercules |
| T-10 | 50.2 | 9 | Hercules |
| N-22 | 47.8 | 20 | Hercules |
| N-4 | 48.6 | 5 | Hercules |
| T-100 | 49.7 | 96 | Hercules |
| K-50 | 46.7 | 51 | Hercules |
| K-50 | 46.3 | 49 | Hercules |
| N-50 | 48.1 | 51 | Hercules |
| N-100 | 47.7 | 95 | Hercules |
| K-14 | 46.2 | 14 | Hercules |
| N-100 | 48.5 | 96 | Hercules |
| T-10 | 49.8 | 9.7 | Hercules |
| K-14 | 46.2 | 13 | Hercules |
| Standard | 48.6 | 45 | Dow |
| Standard | 48.1 | 45 | Dow |
| Standard | 48.4 | 45 | Dow |
| N-50 | 48.5 | 49 | Hercules |
| T-50 | 50.1 | 47 | Hercules |
| T-10 | 49.8 | 9.7 | Hercules |
| T-10 | 50.2 | 9.0 | Hercules |
| T-10 | 50.5 | 8.8 | Hercules |
| T-10 | 49.9 | 10.0 | Hercules |
| T-10 | 50.5 | 10.2 | Hercules |
| T-10 | 50.3 | 9.0 | Hercules |
| T-10 | 49.8 | 11.0 | Hercules |

From the above examples it can be determined that strip devices can be prepared according to the method of the present invention which do not present windowframing problems. In addition ethoxyl content and viscosity of ethyl cellulose are no longer parameters controlling windowframing and performance of strips. Quality product can be manufactured on a consistent basis thereby easing quality control problems. By eliminating the need to control ethoxyl content and viscosity, the types of ethyl cellulose available for use become more extensive. This enables one to select an ethyl cellulose material which possesses other beneficial properties. For example, ethyl cellulose T-10 from Hercules, Inc. is preferred for its high solubility and low viscosity which makes it easy to handle. These properties will also promote uniform coatings due to better impregnation of the filter paper to thereby effect better performance.

What is claimed is:

1. In combination with the method of preparing a test device for the semiquantitative determination of glucose in urine which comprises impregnating a sheet of a bibulous carrier with a solution containing glucose oxidase, a substance having peroxidative activity and a water soluble iodide salt, drying the treated carrier and then saturating the carrier with an organic solution of a film-forming material, drying the carrier to leave a dry residue of the film-forming material and cutting the sheet into test strips, the improvement which comprises the use of a solution containing from about 1.75 to about 4.55 g./100 ml. of ethyl cellulose in a material which will solubilize the ethyl cellulose and will evaporate to leave a uniform residual layer of ethyl cellulose as solvent for the organic solution of film-forming material.

2. The method of claim 1 wherein the solvent is benzene, toluene or a mixture of ethanol and toluene.

3. The method of claim 1 wherein the solvent is a 20/80 (v/v) mixture of ethanol and toluene.

4. The method of claim 1 wherein the ethyl cellulose solution contains from 2.35 to 3.35 g of ethyl cellulose per 100 ml of solvent.

5. The method of claim 1 wherein the bibulous carrier is paper.

6. In combination with the method for the semiquantitative determination of glucose in urine which method comprises contacting the urine with a test device comprising a bibulous carrier impregnated with the residue of a solution containing glucose oxidase, a substance having peroxidative activity and water soluble iodide salt which device is coated with a hydrophobic, semipermeable layer and determining the concentration of glucose in the urine from the color change of the device the improvement therein in which the layer is the dry residue created by saturating the device with a solution containing from about 1.75 to about 4.55 g./100 ml. of ethyl cellulose in a material which will solubilize the ethyl cellulose and will evaporate to leave a uniform residual layer of ethyl cellulose as solvent for the ethyl cellulose and removing the solvent.

7. The method of claim 6 wherein the solvent used to prepare the test device is benzene, toluene or a mixture of ethanol and toluene.

8. The method of claim 7 wherein the solvent is a 20/80 (v/v) mixture of ethanol and toluene.

9. The method of claim 6 wherein the test device is prepared by saturating it with a solution containing from 2.35 to 3.35 g/100 ml of ethyl cellulose in an appropriate solvent.

10. The method of claim 6 wherein the bibulous carrier is paper.

11. In a test device for determining the presence of glucose in a liquid test sample, wherein said device comprises a carrier matrix impregnated with glucose oxidase, a peroxidatively active substance and a water soluble iodide salt, the improvement wherein said carrier matrix is additionally impregnated with ethyl cellulose by saturating said carrier with an organic solution containing about 1.75 to about 4.55 grams of ethyl cellulose per 100 milliliters of solvent.

12. The device of claim 11 wherein the solvent for the ethyl cellulose is benzene, toluene or a mixture of ethanol and toluene.

13. The device of claim 12 wherein the solvent is a 20/80 (v/v) mixture of ethanol and toluene.

14. The device of claim 11 wherein the ethyl cellulose solution contains from 2.35 to 3.35 g of ethyl cellulose per 100 ml of solvent.

15. The device of claim 11 wherein the carrier matrix is paper.

* * * * *